United States Patent
Pyles

[11] Patent Number: 6,136,304
[45] Date of Patent: Oct. 24, 2000

[54] CONDITIONING COMPOSITIONS

[75] Inventor: Daniel Raymond Pyles, Chicago, Ill.

[73] Assignee: Helene Curtis, Inc., Chicago, Ill.

[21] Appl. No.: 09/138,229

[22] Filed: Aug. 21, 1998

[51] Int. Cl.[7] .................................................. A61K 7/075
[52] U.S. Cl. .................................... 424/70.28; 424/70.12; 424/70.121; 424/70.27
[58] Field of Search ........................... 424/70.12, 70.121, 424/70.27, 70.28

[56] References Cited

U.S. PATENT DOCUMENTS

| | | |
|---|---|---|
| 3,993,744 | 11/1976 | Cella et al. . |
| 4,275,055 | 6/1981 | Nachtigal et al. . |
| 4,597,964 | 7/1986 | Ziemelis et al. . |
| 4,654,161 | 3/1987 | Kollmeier et al. .................. 252/174.15 |
| 4,658,839 | 4/1987 | Dallal et al. ................................ 132/7 |
| 4,725,433 | 2/1988 | Matravers . |
| 4,777,037 | 10/1988 | Wagman et al. . |
| 4,954,335 | 9/1990 | Janchipraponvej . |
| 4,976,956 | 12/1990 | Noe ........................................... 424/70 |
| 5,302,322 | 4/1994 | Birtwistle ................ 252/547 |
| 5,306,434 | 4/1994 | Schueller et al. ......................... 252/8.8 |
| 5,328,685 | 7/1994 | Janchipraponvej et al. . |
| 5,332,569 | 7/1994 | Wood et al. ............................... 424/70 |
| 5,556,615 | 9/1996 | Janchitraponvej et al. ......... 424/70.11 |
| 5,759,527 | 6/1998 | Patel et al. ........................... 424/70.11 |

*Primary Examiner*—Thurman K. Page
*Assistant Examiner*—P. E. McQueeney
*Attorney, Agent, or Firm*—Matthew Boxer

[57] ABSTRACT

A method of imparting improved conditioning properties to hair comprising treating the hair with a conditioning composition comprising a silicone compound having at least one quaternary ammonium moiety and ethoxylated monoalkyl quat.

12 Claims, No Drawings

CONDITIONING COMPOSITIONS

FIELD OF THE INVENTION

The present invention relates to conditioning compositions and to a method of treating hair that imparts improved conditioning properties to hair. The conditioning composition can be applied to the hair from an aqueous solution or spray, a conditioner formulation, a hair color or other similar hair treatment product to improve both the wet stage and the dry stage properties of the hair.

BACKGROUND OF THE INVENTION

The present invention is directed to a new conditioning composition that is esthetically acceptable to consumers, improves the wet combing and dry combing properties of hair, and also leaves the dry hair with satisfactory cosmetic and physical properties, including, in particular, dry combing and feel, less hair coating, manageability, body, condition of the ends and set.

Effective clear conditioning compositions have been difficult to formulate because conditioning compounds used in clear conditioning compositions often have a relatively high water solubility and are too easily rinsed from the hair. Formulators of clear conditioners have tried to overcome this by solubilizing water insoluble ingredients such as dialkylquats and dimethicone, but these compositions being highly solubilized have not been effective either. Therefore investigators have sought compositions incorporating a conditioning compound that provides a clear composition yet is not easily rinsed from the hair.

The present invention utilizes water-soluble ingredients that surprisingly are not easily rinsed from the hair, that attach to the hair and condition the hair, providing superior conditioning benefits.

Hair conditioning compositions, such as emulsion-type creme rinses, are well known in the art for improving the combing properties of wet hair and dry hair. These conditioning compositions typically are aqueous emulsions including a cationic compound, like a quaternary ammonium compound, as the principal conditioning agent. Prior patents describe the quaternary ammonium compound either as a polymeric material having a plurality of quaternary nitrogen atoms per molecule or as a molecule having at least one long carbon chain and an average of one quaternary nitrogen atom per molecule. The prior patents also describe hair conditioning compositions as including silicon-containing compounds, substituted amides and amides, nonionic surfactants, long carbon chain alcohols and esters, and other ingredients to facilitate composition formulation and enhance consumer appeal.

For example, Cella et al. U.S. Pat. No. 3,993,744 discloses that cationic compounds, such as quaternary ammonium compounds, and silicones can be combined with perfluorinated compounds to provide hair treatment compositions. The silicones specifically disclosed by Cella et al. are nonionic surfactant-like polyoxyethylene polymethylsiloxanes that apparently are water-soluble or dispersible.

Matravers U.S. Pat. No. 4,725,433 discloses a clear conditioning composition comprising an aqueous blend of a polymeric quaternary ammonium salt, ethoxylated lauryl alcohol, ethoxylated cholesterol and hydroxyethylcellulose.

Ben Janchitraponjev U.S. Pat. No. 4,954,335 discloses a clear conditioning composition comprising a quaternary ammonium compound, an amidoamine, a volatile conditioning agent and a solubilizing nonionic surfactant.

Nachtigal et al. U.S. Pat. No. 4,275,055 discloses a pearlescent hair conditioner composition including a quaternized tertiary amidoamine, a quaternary ammonium compound and, optionally, a tertiary amidoamine, i.e., stearamidoethyidiethylamine. The composition of Nachtigal et al. is directed to achieving a stable pearlescent effect and neither includes a silicone compound having at least one quaternary ammonium moiety nor is the composition a clear conditioning composition.

Wagman et al. U.S. Pat. No. 4,777,037 discloses a hair conditioner composition comprising a polydimethyl cyclosiloxane, a quaternary-nitrogen containing conditioning agent having two long alkyl chains of twelve to eighteen carbons and two short alkyl chains of one or two carbon atoms, a long chain fatty alcohol and a tertiary amidoamine.

Ziemelis et al. U.S. Pat. No. 4,597,964 discloses a cationic polyorganosiloxane that is substantive to protein substrates. The disclosed cationic organosiloxanes are emulsifiable and are used to treat hair.

Ben Janchitraponjev et al U.S. Pat. No. 5,328,685 discloses a method of imparting improved conditioning properties to hair comprising treating the hair with a clear conditioning composition comprising specified amidoamine salts.

As will be demonstrated more fully hereinafter, a conditioning composition of the present invention, comprising a silicone compound having at least one quaternary ammonium moiety and ethoxylated monoalkyl quat imparts improved conditioning properties upon application to human hair. Therefore, the condition of treated hair is improved by a method of contacting the hair with an aqueous conditioning composition comprising a silicone compound having at least one quaternary ammonium moiety and ethoxylated monoalkyl quat. A composition of the present invention can be applied to the hair from an aqueous carrier at ambient temperature and is allowed to contact the hair for a relatively short time to provide the benefits and advantages of a hair conditioner. Consequently, the method and composition of the present invention condition the hair to provide more manageable and esthetically-pleasing hair.

SUMMARY OF THE INVENTION

In brief, the present invention relates to a composition and method of treating hair. More particularly, the present invention relates to a method of treating the hair, whereby the hair is conditioned by contacting the hair with a conditioning composition comprising a silicone compound having at least one quaternary ammonium moiety and ethoxylated monoalkyl quat.

The easy-to-apply composition is esthetically pleasing for consumer acceptance, imparts excellent wet stage and dry stage conditioning properties to the hair, and is easily rinsed from the hair. Surprisingly and unexpectedly, hair treated with a clear conditioner composition of the present invention also demonstrates improved physical and cosmetic properties, such as wet and dry feel, less coating, thickness, overall hair condition, manageability and body.

Therefore, one aspect of the present invention to provide a conditioning composition that conditions the hair and imparts improved physical and cosmetic properties to the hair. The clear conditioning composition is translucent to transparent to improve consumer acceptance, is easily applied to and rinsed from the hair, and deposits a sufficient residual amount of the conditioner on the hair to condition the hair.

Another aspect of the present invention to provide a conditioning composition comprising a silicone compound having at least one quaternary ammonium moiety and ethoxylated monoalkyl quat.

Another aspect of the present invention is to provide a method of treating hair with a conditioning composition to improve the condition of the hair.

Another aspect of the present invention is to provide a method of treating hair by contacting the hair with a clear conditioning composition then drying the hair, to condition the hair and to impart improved physical and cosmetic properties to the hair.

Another aspect of the present invention is to provide a method of treating hair to yield well-conditioned hair by contacting the hair with a conditioning composition comprising a silicone compound having at least one quaternary ammonium moiety and ethoxylated monoalkyl quat.

Another aspect of the present invention is to provide a new and improved conditioning composition capable of conditioning the hair and imparting improved physical, cosmetic and esthetic properties both to normal hair and to tinted, frosted, bleached or other substantially-damaged hair.

Still another aspect of the present invention is to provide a method of treating the hair to yield well-conditioned hair having esthetically-pleasing physical properties by contacting the hair with a aqueous spray or solution to treat the hair, without heat, in either a rinse-off or leave-on method.

DETAILED DESCRIPTION OF THE PREFERRED EMBODIMENT

A conditioning composition of the present invention comprises: a conditioning composition comprising a silicone compound having at least one quaternary ammonium moiety and ethoxylated monoalkyl quat. The easy-to-apply, conditioning composition imparts excellent wet comb and dry comb properties to the hair, and the hair demonstrates improved physical and cosmetic properties, such as gloss, thickness, softness, manageability, body and less coating.

The silicone compound having at least one quaternary ammonium moiety of the compositions of the invention is a cationic organosiloxane of the general structure IV A silicone compound having at least one quaternary ammonium moiety which is used in compositions of the invention can be water soluble or water dispersible. One skilled in the art would determine that such a compound is water soluble by mixing it with water and obtaining a clear solution. One skilled in the art would determine that such a compound is water dispersible by mixing it with water and obtaining a hazy, but homogeneous mixture. If one mixed a silicone compound with water and obtained two layers, the silicone compound would be water insoluble and not suitable for the compositions of the invention.

An example of a water soluble or water dispersible silicone compound having at least one quaternary ammonium moiety is depicted by general structure IV in columns 9 and 10 of U.S. Pat. No. 5,328,685 issued Jul. 12, 1994 which is hereby incorporated by reference. A silicone compound having at least one quaternary ammonium moiety, such as the compound depicted in general formula IV of the U.S. Pat. No. 5,328,685 exhibits properties of a silicone and a quaternary ammonium compound, and imparts conditioning properties to the hair.

A specific example of a silicone compound of general structure IV of U.S. Pat. No. 5,328,685 that is useful in the compositions and the method of the present invention is designated in the CTFA dictionary as quaternium-80, available commercially under the tradename AIL-QUAT 3270 and ABILQUAT 3272 from Goldschmidt Chemical Corporation, Hopewell, Va. and having the structural formula VI of the U.S. Pat. No. 5,328,685.

Other silicone compounds having at least one quaternary ammonium moiety that can be used in the compositions of the invention are disclosed in U.S. Pat. No. 5,098979 incorporated herein by reference. The disclosed silicone compounds are polymers having a silicone backbone with at least one quaternary ammonium moiety as a pendant group. The quaternary ammonium moiety can be an alkylamido group or an imidazoline group.

In particular, the silicone compounds disclosed in O'Lenick, Jr. U.S. Pat. No. 5,098,979 in formula (XII) may be included in the compositions of the invention. O'Lenick, Jr., U.S. Pat. No. 5,098,979 is hereby incorporated by reference.

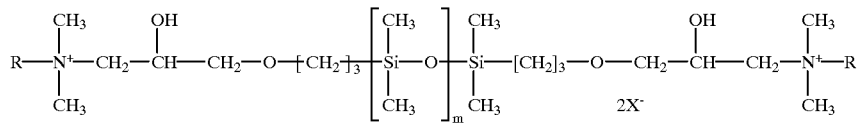 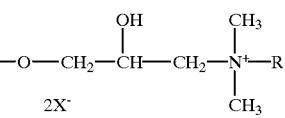

wherein R is an alkyl group having one to about 22 carbon atoms, m is a numeral from about 5 to about 50, and X is a water soluble anion,
or more specifically having the structural formula VI Silicone compounds depicted by formula (XII) of O'Lenick, Jr. U.S. Pat. No. 5,098,979 are available commercially from Siltech Inc., Norcross, Ga. under the tradename SILQUAT. Particular silicone compounds of formula

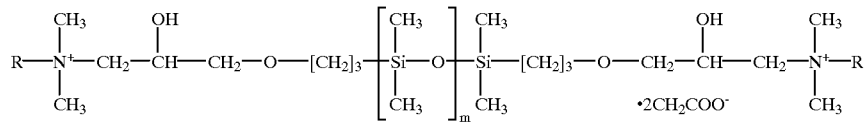 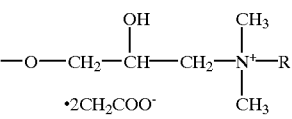

wherein R is an alkyl group having 1 to about 22 carbon atoms and m is an integer from about 5 to about 30, or a silicone polymer having at least one pendant quaternary ammonium moiety, or a mixture thereof.

(XII) are SILQUAT Q-100, SILQUAT Q-200, and SILQUAT Q-300 and Silquat 400. These Silquats are water-dispersible and with a small amount of the ethoxylated monoalky quat yield a clear conditioner. The SILQUAT silicone compounds differ primarily in the moles of ethoxylation and/or propoxylation present in the compound. SILQUAT Q-50 is not water-dispersible having the fewest moles of ethoxylation and/or propoxylation in comparison to the other SILQUAT silicone compounds and therefore needs high levels of coupling (solubilizing) agents to get a clear conditioner. This high solubilization often renders the water-insoluble ingredient, that is SILQUAT Q-50, ineffective in clear conditioners.

The silicone compound, having at least one quaternary ammonium moiety of the compositions of the invention are described in U.S. Pat. No. 5,328,685 issued Jul. 12, 1994 which is hereby incorporated by reference.

The ethoxylated monoalkyl quat of the compositions of the invention can have from about 1 to about 50 moles of ethoxylation, or more preferably, about 0.5 to about 20 moles of ethoxylation. Exemplary of the ethoxylated monoalkyl quats of the invention are:

PEG-2 Olealmonium Chloride;

PEG-2 Cocomonium Chloride;

PEG-15 Cocomonium Chloride;

PEG-15 Stearmonium Chloride;

PEG-2 Tallowmonium Chloride;

and the like.

In addition to the above-described essential ingredients, other common cosmetic components and additives can be incorporated in the conditioning composition with the essential ingredients, as long as the basic properties of the composition, and an ability to condition the hair, are not adversely affected. Such optional ingredients include, but are not limited to, humectants, emollients, moisturizers, inorganic salts, fragrances, dyes, hair colorants, hydrotropes, foam stabilizers, preservatives, water softening agents, acids, bases, buffers and the like. Optional components usually are present in weight percentages of less than about 2% each, and from about 5% to about 10% by weight of the composition in total.

Other optional ingredients can be included in the conditioning composition to enhance the ability of the composition to condition the hair. For example, other quaternary ammonium compounds can be included in the conditioning composition. A quaternary ammonium compound useful in the composition of the present invention preferably is a water-soluble quaternary ammonium compound having one or two long chain alkyl groups containing from about 8 to about 18 carbon atoms. The long chain alkyl groups also can include, in addition to, or as a substitute for, carbon and hydrogen atoms, ether linkages or similar water-solubilizing linkages. The remaining two to three substitutes of the quaternary nitrogen of the quaternary ammonium compound can be hydrogen; or benzyl; or short chain alkyl or hydroxyalkyl groups such as methyl, ethyl, hydroxymethyl or hydroxyethyl groups; or mixtures thereof, either of the same or of different identity. However, an oil-soluble, water dispersible quaternary ammonium compound, either alone or in combination with a water-soluble quaternary ammonium compound, also can be used in the composition of the present invention.

An optional quaternary ammonium compound is dicetyidimonium chloride, available commercially from Sherex Chemical Co., Dublin, Ohio, under the tradename ADOGEN 432-ET. Other useful quaternary ammonium compounds include lauryltrimethylammonium chloride, stearyltri(2-hydroxyethyl)ammonium chloride, lauryldimethylbenzylammonium chloride, oleyldimethylbenzylammonium chloride, dilauryldimethylammonium chloride, cetyldimethylbenzylammonium chloride, dicetyldimethylammonium chloride, laurylpyridinium chloride, and cetylpyridinium chloride. A quaternized protein- based quaternary ammonium compound, such as a quaternized wheat-based protein sold under the tradename MACKPRO WLW, available from The McIntyre Group, University Park, Ill., also can be used in the present conditioning composition.

An optional thickener also can be included in the clear or opaque conditioning composition to improve composition esthetics and facilitate application of the composition to the hair. Nonionic thickeners in an amount of 0% to about 3% by weight are preferred. Exemplary thickeners are methylcellulose, hydroxybutyl methylcellulose, hydroxypropylcellulose, hydroxypropyl methylcellulose, hydroxyethyl ethylcellulose and hydroxyethylcellulose, di(hydrogenated tallow)phthalic acid amide, crosslinked maleic anhydride-methyl vinyl ether copolymer, guar gum, xanthan gum and gum arabic.

The carrier of the conditioning composition is predominantly water, but organic solvents also can be included in order to facilitate manufacturing of the composition or to provide esthetic properties, such as viscosity control. Suitable solvents include the lower alcohols like ethyl alcohol and isopropyl alcohol; glycol ethers, like 2-butoxyethanol, ethylene glycol monoethyl ether, propylene glycol and diethylene glycol monoethyl ether or monomethyl ether; and mixtures thereof. Non-aqueous solvents can be present in the conditioning composition of the present invention in an amount of about 1% to about 50%, and in particular about 5% to about 25%, by weight of the total weight of the carrier in the composition.

A composition of the present invention is a composition that is stable to phase or ingredient separation at a temperature of about 25° C. for an indefinite period of time. For example, a conditioning composition of the present invention has demonstrated sufficient stability to phase and ingredient separation at temperatures normally found in commercial product storage and shipping to remain unaffected for periods of one year or more.

Treating the hair with the compositions of the invention is carried out by conditioning the hair, that is, (1) applying water to said hair (or starting the process with hair that is damp because it has already been shampooed); (2) applying to said an effective amount of a conditioning composition of the invention; (3) rubbing said hair with the hands or a hair appliance such as a comb; and (4) rinsing said hair with water.

A clear, viscous composition has enhanced consumer appeal compared to the present-day, emulsion-type conditioner compositions. The present clear conditioning composition also deposits a sufficient amount of the conditioning compounds on the hair to condition the hair. Previous clear conditioning compositions often did not sufficiently condition the hair because clarity was achieved by using water soluble ingredients, including conditioning compounds, that were easily rinsed from the hair, or used water insoluble ingredients that were highly solubilized, therefore being easily rinsed from the hair and ineffective. The present compositions provide both consumer-preferred clarity and good hair conditioning. More specifically, the compositions of the present invention employ water soluble agents that would be expected to be easily rinsed from the hair, but surprisingly, the compositions of the invention, instead have been found to be effective as hair conditioners.

Clear hair conditioning compositions of the invention are made according to methods which are known in the art. Starting materials for preparing these compositions of the invention are either known or can be made by known methods.

Description of how compositions of the invention are made.

Step 1. The solvent carrier water is added to a suitable tank;

Step 2. Moderate agitation is begun;

Step 3. Hydroxyethyl cellulose is dispersed until fully dissolved;

Step 4. Heat tank up to 120–125 F;

Step 5. Turn of heat allow batch to cool to 100–100 F;

Step 5. PEG-2 Olealmonium Chloride is added to tank. Mix until uniform;

Step 6. Liquid Citric Acid, 50% is added to tank.

Step 7. Add Quaternium-80; Mix until uniform;

Other optional ingredients can be added as long as they do not decrease the clarity and conditioning performance of the present invention.

Therefore, the method and composition of the present invention impart hair conditioning properties to treated hair as well as or better than present day clear conditioning compositions and as well as or better than emulsified conditioner compositions. It is both surprising and unexpected for an aqueous composition of the present invention to be a consumer-appealing clear product, to maintain product stability over long storage times, and to impart with such excellent hair conditioning properties to treated hair. The clear compositions of the present invention sufficiently coat the hair with conditioning agents and also are easy to rinse from the hair.

In addition, the method of the present invention provides the further benefits of not leaving the hair tacky or sticky; not forming a crust and therefore providing combability; and providing manageable and styleable hair having body. In addition, after treating the hair with the composition of the present invention, the hair feels natural and thickened, has body, is soft, shiny, manageable and combable. These beneficial effects can be achieved by using an aqueous spray or aqueous solution formulation.

Table 1 shows compositions of the invention.

TABLE 1

| Ingredient (As Is) | Composition | |
|---|---|---|
| | A | B |
| Deionized Water | Q.S. | Q.S. |
| Hydroxyethyl cellulose | 1.3 | |
| PEG-2 Olealmonium Cl & Propylene Glycol | 2.5 | 2.5 |
| Cetrimonium Cl | 2 | — |
| Quaternium-80 | 2 | 2 |
| Disodium EDTA | .1 | — |
| Kathon CG[1] | .05 | — |
| DMDM Hydantoin | .1 | — |
| Benzophenone-4 | .05 | — |
| Fragrance | .4 | — |
| Polysorbate-20 | .4 | — |
| Liquid Citric Acid, 50% | .065 | .065 |

[1]Rohm & Haas

TABLE 2

| Instron Wet Combing and Static Charge Build-up Studies | | | | |
|---|---|---|---|---|
| Ingredients | C | D | E prior art | F prior art |
| Deionized Water | Q.S* | Q.S. | | |
| Hydroxyethylcellulose | 1 | 1.3 | | |
| Stearamidopropyl Dimethylamine | — | .75 | | |
| PEG-2 Olealmonium Chloride (69% active) & Propylene Glycol (31% active) | — | 2.5 | | |
| Propylene Glycol, USP | — | 1 | | |
| Cetrimonium Chloride, 30% active | 2 | 2 | | |
| Quaternium-80, 50% active | 2 | 2 | | |
| FD&C Blue #1, 85% active | .00003 | .00003 | | |
| Disodium EDTA | .1 | .1 | | |
| Kathon CG[1] | .08 | .05 | | |
| DMDM Hydantoin | .1 | | | |
| Crodarom Complex HC[2] | .001 | — | | |
| Benzophenone-4 | .05 | .05 | | |
| Fragrance | .4 | .4 | | |
| PEG-15 Nonyl Phenyl Ether | .4 | .4 | | |
| Liquid Citric Acid, 50% active | .1 | .34 | | |
| odium Hydroxide, 50% active | .05 | — | | |
| Combing Force (g force) | 12.5EF* | 7.5CEF* | 16.0 | 15.0 |
| Absolute Static Build-up (kV/m) | 115.7 | 9.CEF* | 45.1C* | 36.4C* |

[1]Rohm & Haas
[2]Croda, Inc., Parsippany, N.J.
A product with a letter next to it means that it is significantly better than that product at a 95% C.I.

SUMMARY

Formula D is significantly preferred in both wet combing and static charge build-up versus Formula C, Formula E and Formula F. Both Prell Extra Body (Formula E) and Pantene Pro-V Normal (Formula F) are opaque conditioners, while HCSS Daily Clarifying (Formula C) is a clear conditioner.

Formula D is preferred over Formula C because Formula D contains the ingredient PEG-2 Olealmonium Chloride which works in synergy with the Quaternium-80 to both decrease wet combing force and static charge build-up.

TABLE 3

The Instron combing test and combing force are as described in Garcie et al. J. Soc. Cosmet. Chem. 27:379 (1976) which is hereby incorporated by reference. Static charge test methods and the definition of static charge are as described in Lunn et al. J. Soc. Cosmet. Chem. 28:549 (1977) which is hereby incorporated by reference.

| Instron Wet Combing and Static Charge Build-Up Studies | | | | |
|---|---|---|---|---|
| Ingredients | C | G | H | I |
| Deionized Water | Q.S. | Q.S. | Q.S. | Q |
| Hydroxyethyl cellulose | 1 | 1.3 | 1.2 | 1.3 |
| Polyquaternium-10 | — | — | .15 | — |
| Isostearamidopropyl Morpholine Lactate, 25% active | — | 2 | — | — |
| PEG-2 Olealmonium Chloride (69% active) & Propylene Glycol (31% active) | — | 1.5 | 1.5 | 1.5 |

-continued

Instron Wet Combing and Static Charge Build-Up Studies

| Ingredients | C | G | H | I |
|---|---|---|---|---|
| Propylene Glycol, USP | — | 2 | 2 | 2 |
| Cetrimonium Chloride, 30% active | 2 | 2 | 2 | 2 |
| Quaternium-80, 50% active | 2 | 1.5 | 1.5 | 1 |
| FD&C Blue #1, 85% active | .00003 | .00003 | .00003 | .00003 |
| Disodium EDTA | .1 | .1 | .1 | .1 |
| Kathon CG[1] | .08 | .05 | .05 | .05 |
| DMDM Hydantoin | .1 | .1 | .1 | .1 |
| Crodarom Complex HC[2] | .001 | — | — | — |
| Benzophenone-4 | .05 | .05 | .05 | .05 |
| Fragrance | .4 | .4 | .4 | .4 |
| PEG-15 Nonyl Phenyl Ether, 99.5% active | .4 | .4 | .4 | .4 |
| Liquid Citric Acid, 50% active | .1 | .045 | — | .045 |
| odium Hydroxide, 50% active | .05 | — | — | — |
| Combing Force (g force) | 11.2 | 6.8C | 6.7C | 5.1CG |
| Absolut Static Build-up (kV/m) | 86.9 | 30.45 | 16.6C | 17.0C |

[1]Rohm & Haas
[2]Croda, Inc., Parsippany, N.J.

In Table 2, formula D was significantly better than formula C. Formula D contains an amidoamine, Stearamidopropldimethylamine which becomes an amine salt when neutralized. Table 3 proves that the amine or amine salt is not necessary in the formulation and may actually decrease conditioning performance when included in the compositions of the invention, Formula I Formula I without the amine salt, Isostearamidopropyl Morpholine Lactate, is significantly preferred over Formula G which contains the amine salt, Isostearamidopropyl Morpholine Lactate. Isostearamidopropyl Morpholine Lactate is well known in the art as a mild conditioning agent used in such products as hand soaps. It should not deter conditioning. This study shows that the present invention does not need amidoamines or amine salts to gain the desirable performance. The combination of PEG-2 Olealmonium Chloride & Quaternium-80 is necessary. Formula H shows that the inclusion of a cationic polymer does not increase the wet combability of, Formula I, a formulation of the present invention.

TABLE 4

Instron Wet Combing and Static Charge Build-Up Studies

| Ingredients | C | D | I |
|---|---|---|---|
| Deionized Water | Q.S. | Q.S | Q.S. |
| Hydroxyethyl cellulose | 1 | 1.3 | 1.3 |
| Stearamidopropyl Dimethylamine | — | .75 | — |
| PEG-2 Oleatmonium Chloride (69% active) & Propylene Glycol (31% active) | — | 2.5 | 1.5 |
| Propylene Glycol, USP | — | 1 | 2 |
| Cetrimonium Chloride, 30% active | 2 | 2 | 2 |
| Quaternium-80, 50% active | 2 | 2 | 1.5 |
| FD&C Blue #1, 85% active | .00003 | .00003 | .00003 |
| Disodium EDTA | .1 | .1 | .1 |
| Kathon CG[1] | .08 | .05 | .05 |
| DMDM Hydantoin | .1 | .1 | .1 |
| Crodarom Complex HC[2] | .001 | — | — |
| Benzophenone-4 | .05 | .05 | .05 |
| Fragrance | .4 | .4 | .4 |
| PEG-15 Nonyl Phenyl Ether | .4 | .4 | .4 |
| Liquid Citric Acid, 50% active | .1 | .34 | .045 |
| Sodium Hydroxide, 50% active | .05 | — | — |
| Combing Force (g force) | 12.6 | 8.0C | 6.9C |
| Absolute Static Build-up (kV/m) | off scale | 5.5C | 17.2C |

[1]Rohm & Haas
[2]Croda, Inc., Parsippany, N.J.

This study shows that formula I without amidoamine or amine salt performs similarly to formula D with amidoamine (amine salt when neutralized in the formula). Clearly the amine salt does not contribute any conditioning effect to the "present invention".

In all three studies formula C has been included. This formula is similar to a commercial formula. All three studies show that while all the formula have at least 1.5% Quaternium-80, the inclusion of the PEG-2 Olealmonium Chloride gives the "present invention" a significant wet combing and static charge build-up advantage versus formula C.

TABLE 5

| Ingredients | C | J |
|---|---|---|
| Salon Descriptive Half Head Studies (N = 6) Salon Study | | |
| Deionized Water | Q.S. | Q.S. |
| Hydroxyethyl cellulose | 1 | 1.1 |
| Stearamidopropyl Dimethylamine | — | .75 |
| PEG-2 Olealmonium Chloride (69% active) & Propylene Glycol (31% active) | — | 2.5 |
| Propylene Glycol, USP | — | 1 |
| Cetrimonium Chloride, 30% active | 2 | 2 |
| Quaternium-80, 50% active | 2 | 2 |
| FD&C Blue #1, 85% active | .00003 | .00003 |
| Disodium EDTA | .1 | .1 |
| Kathon CG[1] | .08 | .05 |
| DMDM Hydantoin | .1 | .1 |
| Crodarom Complex HC[2] | .001 | — |
| Benzophenone-4, 100% active | .05 | .05 |
| Fragrance | .4 | .4 |
| PEG-15 Nonyl Phenyl Ether | .4 | .4 |
| Liquid Citric Acid, 50% active | .1 | .35 |
| odium Hydroxide, 50% active | .05 | — |
| Salon Descriptive Study Average | | |
| Wet Detangling (Formula J preferred 3 out of 6 heads with 1 head even) | 7.6 | 7.9 |
| Wet Combing (Formula J preferred 4 out of 6 heads) | 7.7 | 8.1 |
| Wet Feel (Formula J preferred 6 out of 6 heads) | 4.9 | 5.5 |
| Dry Combing (Formula J preferred 4 out of 6 heads) | 5.8 | 6.0 |
| Dry Feel (Formula J preferred 3 out of 6 heads, with 1 head even) | 5.1 | 5.3 |
| Sheen (Formula J preferred 2 out of 6 heads with 3 heads even) | 8.2 | 8.4 |
| Static (Formula J preferred 2 out of 6 heads with 4 heads even) | .7 | .3 |

[1]Rohm & Haas
[2]Croda, Inc., Parsippany, N.J.

This study shows that Formula J with 2.5% PEG-2 Olealmonium Chloride and 2% Quaternium-80, is a superior conditioner versus Formula C with only the 2% Quaternium-80.

TABLE 6

| Ingredients | K | J |
|---|---|---|
| Salon Descriptive Half Head Studies (N = 6) Salon Study | | |
| Soft Water | Q.S. | — |
| Deionized Water | — | Q.S. |
| Hydroxyethyl cellulose | — | 1.1 |
| PEG-2 Olealmonium Chloride (69% active) & Propylene Glycol (31% active) | — | 2.5 |
| Propylene Glycol, USP | .5 | 1 |
| Stearamidopropyl Dimethylamine | .5 | .75 |
| Dicetyldimonium Chloride (68% active) & Propylene Glycol, (27% active) | 2.1 | — |

TABLE 6-continued

| Ingredients | K | J |
|---|---|---|
| Cetrimonium Chloride, 30% active | — | 2 |
| Quaternium-80, 50% active | — | 2 |
| Stearyl Alcohol (70% active) & Ceteareth-20 (30% active) | 1 | — |
| D&C Green #5, 80% active | .000263 | — |
| FD&C Blue #1, 85% active | — | .00003 |
| Cetyl Alcohol | 3.25 | — |
| Potassium Chloride, USP/FCC | .1 | — |
| Disodium EDTA | .1 | .1 |
| Kathon CG[1] | .08 | .05 |
| DMDM Hydantoin | .1 | .1 |
| Crodarom Complex HC[2] | .001 | — |
| Benzophenone-4 | — | .05 |
| Cyclomethicone | 1.8 | — |
| Dimethicone | .1 | — |
| Fragrance | .3 | .4 |
| PEG-15 Nonyl Phenyl Ether | — | .4 |
| Liquid CitricAcid, 50% active | .185 | .35 |
| Potassium Hydroxide, Liquid 50% active | .0334 | — |
| Salon Descriptive Study Average | | |
| Wet Detangling (Formula J preferred 4 out of 6 heads) | 7.3 | 7.0 |
| Wet Combing (Formula J preferred 4 out of 6 heads) | 7.8 | 7.5 |
| Wet Feel (Formula J preferred 4 out of 6 heads with 1 head even) | 6.0 | 5.6 |
| Dry Combing (Formula J preferred 2 out of 6 heads with 1 head even) | 6.6 | 6.4 |
| Dry Feel (Formula J preferred 4 out of 6 heads) | 5.7 | 5.3 |
| Sheen (Formula J preferred 2 out of 6 heads with 4 heads even) | 8.5 | 8.3 |
| Static (Formula J preferred 1 out of 6 heads with 5 heads even) | 0 | .2 |

[1]Rohm & Haas
[2]Croda, Inc., Parsippany, N.J.

This study shows that Formula J, with 2.5% PEG-2 Olealmonium Chloride & 2% Quaternium-80 is a better conditioner overall than Formula K with 2.1% Dicetyidimonium Chloride, 1.8% Cyclomethicone and ~4% Fatty Alcohol. Formula K is a commercial product.

Obviously, many modifications and variations of the invention as hereinbefore set forth can be made without departing from the spirit and scope thereof.

What is claimed is:

1. A hair conditioning composition comprising:
   (a) a silicone compound having at least one quaternary ammonium moiety;
   (b) ethoxylated monoalkyl quaternary ammonium compound, the phrase having about 0.5 to about 20 moles of ethoxylation; and
   (c) an aqueous carrier.

2. The composition of claim 1 wherein said silicone compound having at least one quaternary ammonium moiety is a cationic organosiloxane of the general structure IV

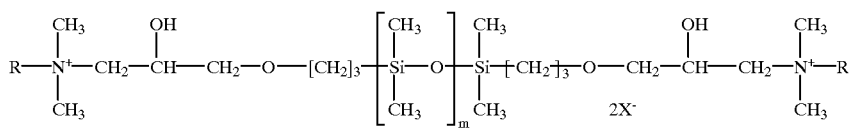

wherein R is an alkyl group having 1 to about 22 carbon atoms and m is an integer from about 5 to about 30, or a silicone polymer having at least one pendant quaternary ammonium moiety, or a mixture thereof.

3. The composition of claim 1 wherein said silicone compound having at least one quaternary ammonium moiety is ABIL-QUAT 3270 or ABILQUAT 3272.

4. The composition of claim 1 wherein said silicone compound having at least one quaternary ammonium moiety is selected from the group consisting of SILQUAT Q-100, SILQUAT Q-200, SILQUAT Q-300 and SILQUAT Q-400.

5. The composition of claim 1 wherein said ethoxylated monoalkyl quat has from about 1 to about 50 moles of ethoxylation.

6. The composition of claim 1 wherein said ethoxylated monoalkyl quat is selected from the group consisting of
   PEG-2 Olealmonium Chloride;
   PEG-2 Cocomonium Chloride;
   PEG-15 Cocomonium Chloride;
   PEG-15 Stearmonium Chloride; and
   PEG-2 Tallowmonium Chloride.

7. The composition of claim 1 which further comprises a quaternary ammonium compound which is a water-soluble and has one or two long chain alkyl groups containing from about 8 to about 18 carbon atoms wherein said long chain alkyl groups can have an ether linkage or other water-solubilizing linkages. and the remaining two to three substituents of the quaternary nitrogen of the quaternary ammonium compound can be hydrogen; or benzyl; or short chain alkyl or hydroxyalkyl groups such as methyl, ethyl, hydroxymethyl or hydroxyethyl groups; or mixtures thereof, either of the same or of different identity.

8. The composition of claim 1 which is clear.

9. The composition of claim 6 which further comprises ingredients selected from the group consisting of humectants, inorganic salts, fragrances, dyes, hair colorants, foam stabilizers, preservatives, water softening agents, acids, bases, and buffers.

10. A composition according to claim 1 which further comprises a thickener selected from the group consisting of methylcellulose, hydroxybutyl methylcellulose, hydroxypropylcellulose, hydroxypropyl methylcellulose, hydroxyethyl ethylcellulose, hydroxyethylcellulose, di(hydrogenated tallow)phthalic acid amide, crosslinked maleic anhydride-methyl vinyl ether copolymer, guar gum, xanthan gum and gum arabic.

11. A composition according to claim 1 which further comprises an organic solvent selected from the group consisting of ethyl alcohol, isopropyl alcohol, 2-butoxyethanol, ethylene glycol monoethyl ether, propylene glycol diethylene glycol monoethyl ether or monomethyl ether; and mixtures thereof.

12. A method of conditioning hair which comprises
(1) applying water to said hair;
(2) applying to said hair an effective amount of a conditioning composition according to claim 1;
(3) rubbing said hair with the hands or a hair appliance such as a comb; and
(4) rinsing said hair with water.

* * * * *

UNITED STATES PATENT AND TRADEMARK OFFICE
CERTIFICATE OF CORRECTION

PATENT NO. : 6,136,304　　　　　　　　　　　　　　　　　　　　　Page 1 of 1
DATED : October 24, 2000
INVENTOR(S) : Daniel Raymond Pyles It is certified that error appears in the above-identified patent and that said Letters Patent is hereby corrected as shown below:

Column 12,
Line 11, please delete the words "the phrase".

Signed and Sealed this

Thirtieth Day of October, 2001

Attest:

*Attesting Officer*

NICHOLAS P. GODICI
*Acting Director of the United States Patent and Trademark Office*